US010401302B2

(12) United States Patent
Röckle

(10) Patent No.: US 10,401,302 B2
(45) Date of Patent: Sep. 3, 2019

(54) INSTALLATION FOR OPTICALLY EXAMINING SURFACE REGIONS OF OBJECTS

(71) Applicant: EISENMANN SE, Böblingen (DE)

(72) Inventor: Jürgen Röckle, Magstadt (DE)

(73) Assignee: EISENMANN SE (DE)

( * ) Notice: Subject to any disclaimer, the term of this patent is extended or adjusted under 35 U.S.C. 154(b) by 0 days.

(21) Appl. No.: 15/961,822

(22) Filed: Apr. 24, 2018

(65) Prior Publication Data

US 2018/0306727 A1 Oct. 25, 2018

(30) Foreign Application Priority Data

Apr. 25, 2017 (DE) .......................... 10 2017 108 770

(51) Int. Cl.
*G01M 11/08* (2006.01)
*G01N 21/88* (2006.01)
(Continued)

(52) U.S. Cl.
CPC ....... *G01N 21/8806* (2013.01); *G01M 11/081* (2013.01); *G01N 21/8803* (2013.01);
(Continued)

(58) Field of Classification Search
CPC .......................... G01N 21/8806; G01M 11/081
(Continued)

(56) References Cited

U.S. PATENT DOCUMENTS 4,847,927 A * 7/1989 Blanc .................... B65F 1/0066
4/629
4,918,321 A * 4/1990 Klenk .................... G01B 11/00
250/559.05
(Continued)

FOREIGN PATENT DOCUMENTS

DE 195 34 145 A1 4/1996
DE 197 30 885 A1 1/1999
(Continued)

OTHER PUBLICATIONS

German Search Report, Request for Search Under Sec. 43 Patent Law (PatG) for German Patent Application No. DE 10 2017 108 770.2, dated Apr. 25, 2017, 15 pages (including English translation).

*Primary Examiner* — Roy M Punnoose
(74) *Attorney, Agent, or Firm* — Haynes and Boone, LLP

(57) ABSTRACT

In various examples, an installation is provided for optically examining surface regions of objects, in particular of painted vehicle bodies, having a test light apparatus for irradiating an object, which is situated in a test region of the installation, with test light and/or for producing a test pattern on the surface region, wherein the test light apparatus has a light-emitting system having a plurality of light-emitting units for emitting test light into the test region, wherein the light-emitting units have a transparent cover with respect to the test region. An operator apparatus is arranged, as viewed from the test region, behind the transparent cover and is set up such that the operator apparatus can be operated by touching at least one section of the cover or/and by (Continued)

approaching such a section. A light-emitting system for such an installation and to a test light module for assembling such an installation are provided.

7 Claims, 3 Drawing Sheets

(51) Int. Cl.
  *G01N 21/89* (2006.01)
  *G01N 21/95* (2006.01)
  *G01M 17/007* (2006.01)
(52) U.S. Cl.
  CPC ..... *G01N 21/8914* (2013.01); *G01N 21/9515* (2013.01); *G01M 17/007* (2013.01)
(58) Field of Classification Search
  USPC .......................................................... 356/610
  See application file for complete search history.

(56) References Cited

U.S. PATENT DOCUMENTS

| | | | |
|---|---|---|---|
| D331,063 S * | 11/1992 | Pasierb | D14/140 |
| 5,201,954 A * | 4/1993 | Holt | B05B 14/40 |
| | | | 118/309 |
| 5,636,024 A | 6/1997 | Crookham et al. | |
| 5,726,705 A * | 3/1998 | Imanishi | G01N 21/8806 |
| | | | 348/92 |
| 5,911,500 A | 6/1999 | Barnett et al. | |
| 6,266,138 B1 * | 7/2001 | Keshavmurthy | G01B 11/303 |
| | | | 356/237.2 |
| 6,320,654 B1 | 11/2001 | Alders et al. | |
| 6,532,066 B1 * | 3/2003 | Filev | G01N 21/8422 |
| | | | 348/92 |
| 7,020,580 B2 * | 3/2006 | Peters | G06F 11/321 |
| | | | 702/183 |
| 2003/0039116 A1 * | 2/2003 | Belair | F21S 2/00 |
| | | | 362/145 |
| 2011/0273375 A1 * | 11/2011 | Wilford | H03K 17/962 |
| | | | 345/173 |
| 2013/0057678 A1 * | 3/2013 | Prior Carrillo | G01N 21/8806 |
| | | | 348/125 |
| 2016/0097725 A1 | 4/2016 | Porter et al. | |
| 2017/0047929 A1 * | 2/2017 | Banfield | H03K 17/962 |
| 2018/0195972 A1 * | 7/2018 | Rockle | G01M 11/081 |

FOREIGN PATENT DOCUMENTS

| | | |
|---|---|---|
| DE | 10 2007 037 943 A1 | 2/2009 |
| DE | 10 2015 116 144 A1 | 4/2016 |
| DE | 10 2015 008 409 A1 | 1/2017 |
| DE | 10 2015 006 012 A1 | 2/2017 |
| WO | WO 2011144964 A1 | 11/2011 |

\* cited by examiner

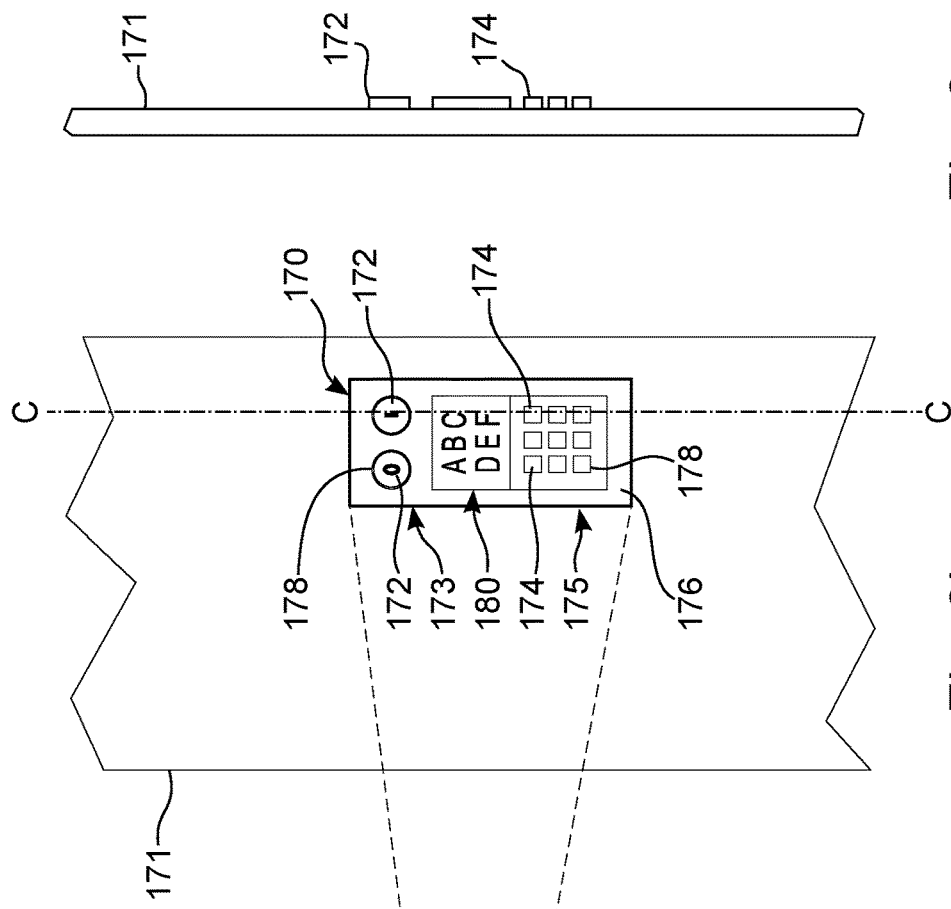
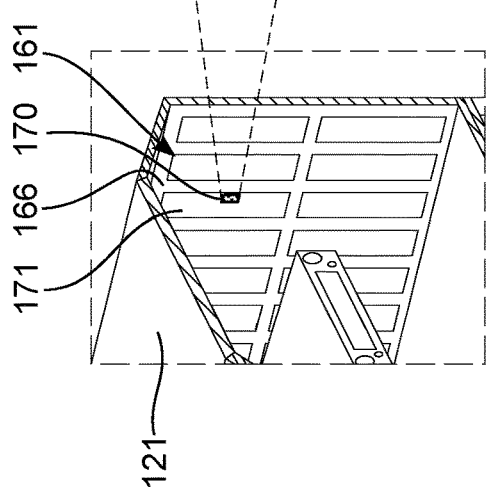
Fig. 3a Fig. 3b Fig. 3c

INSTALLATION FOR OPTICALLY EXAMINING SURFACE REGIONS OF OBJECTS

CROSS-REFERENCE TO RELATED APPLICATIONS

This application claims priority to and the benefit of German Patent Application No. 10 2017 108 770.2 filed Apr. 25, 2017 which is hereby incorporated by reference in its entirety.

BACKGROUND OF THE INVENTION

1. Field of the Invention

The invention relates to an installation for optically examining surface regions of objects, in particular of painted vehicle bodies.

2. Description of the Prior Art

In installations of this type, in particular the surfaces of painted vehicle bodies are visually examined by inspectors in respect of quality. Defects in the surface result in local distortions of a test pattern that is projected onto the vehicle body as compared to a projection of the same test pattern onto a surface that is ideally free from defects. In this way, an experienced inspector will quickly notice any surface defects that are present and can mark them in a suitable fashion.

A large number of different surface defects can occur during the painting process. Such surface defects in painted surfaces can be assigned to different categories. Merely by way of example, and not exhaustively, such surface defects can be paint inclusions, wetting or distribution disturbances, craters, clouding, colour deviations and the like.

When observing the surface of the painted vehicle body, it may be necessary to change the emission of the test light for a more accurate assessment. For example, it may be necessary for individual light-emitting units to be switched on or off or/and for the entire illumination situation within the test region to be adapted. For this purpose, control panels can be provided, for example, for actuating the individual light-emitting units of the test region or the entire test region. However, if the accurate assessment of the surface requires incremental adaptation of the illumination situation, this can mean a process which demands a great deal of walking for the inspector. For each control command, the inspector must walk to the nearest control panel, give the control command, and perform the assessment again.

SUMMARY OF THE INVENTION

The invention relates to an installation for optically examining surface regions of objects, in particular of painted vehicle bodies, having a) a test light apparatus for irradiating an object, which is situated in a test region of the installation, with test light and for producing a test pattern on the surface region, wherein b) the test light apparatus has a light-emitting system having a plurality of light-emitting units for emitting test light into the test region, wherein the light-emitting units have a transparent cover with respect to the test region.

The invention furthermore relates to a light-emitting system for such an installation having at least one first and one second light-emitting device and a test light module for assembling such an installation.

It is an embodiment of the invention to specify an installation of the type mentioned in the introductory part, in which the effectivity and efficiency of the examination are improved over the prior art.

This embodiment is achieved by way of an installation in accordance with independent claim 1.

The installation according to an embodiment of the invention for optically examining surface regions of objects, in particular of painted vehicle bodies, has a test light apparatus for irradiating an object, which is situated in a test region of the installation, with test light. The test light apparatus additionally serves for producing a test pattern on the surface region. The test light apparatus has a light-emitting system having a plurality of light-emitting units for emitting test light into the test region. The light-emitting units are provided with a transparent cover with respect to the test region.

Provision is made according to an embodiment of the invention for an operator apparatus to be provided which is arranged behind the transparent cover of a light-emitting unit, as viewed from the test region. The operator apparatus is set up such that the operator apparatus can be operated, for example, by an inspector touching at least one section of the cover or/and for example by an inspector approaching such a section.

It is possible in this way for an inspector to operate the operator apparatus by way of a simple hand motion in the direction of the cover of a light-emitting unit, directly at the location at which said inspector tests the surface region of the object to be examined and to influence for example the light situation provided for the test. The need to walk to the nearest control panel is dispensed with. At the same time, mounting the operator apparatus within the transparent cover offers the advantage that no edges are formed within the test region due to mounting of the operator apparatus. Since dust or other impurities potentially can easily amass at edges, this makes possible a surface that is easy to clean. Errors in the cleaning of such edges result in inadvertent carryover of the impurities and consequently possibly to a contamination of the coating operation. The inner surface of the test region is therefore easy to clean and the operator apparatus is easy to operate.

As a further advantage, the operator apparatus that is embodied in this way can be designed without mechanical buttons. The associated mechanical wear is dispensed with.

In an advantageous embodiment, provision is made for the operator apparatus to comprise a capacitive sensor.

This has the advantage that many customary, electrically insulating materials, such as in particular glass, can be penetrated by the electric field of the capacitive sensor, with the result that the capacitive sensor can be mounted on the rear side, i.e. the side that is remote from the test region, of the cover. In this way, the side of the cover that faces the test region is unchanged and in particular does not produce edges or seams.

In an advantageous embodiment of the installation, provision may be made for the operator apparatus to be arranged in a region of the light-emitting unit that is not intended for an emission of test light in the direction of the test region. Such a region can be, for example, the environment of a control board that was already present for the light-emitting unit. The transparent cover is preferably embodied in this region such that it is not transparent.

Alternatively or additionally, the region of the cover of the light-emitting unit provided for the operator apparatus can be optically marked for the inspector. This can be done for example by way of marking it in a different colour.

In one embodiment of the invention, provision is made for the operator apparatus to have a display field that is arranged behind the transparent cover and is set up to display information relevant for operating the operator apparatus. It is thus possible for example to display the current light scenario to the inspector before the operator apparatus is operated. Moreover, it is possible for example to display what it is that is triggerable by operating the operator apparatus.

In one embodiment of the invention, provision is made for the operating element to be designed such that one or more of the following processes is/are triggerable by operating the operating element:

switching the emission of test light into the test region on and off; or/and activating a specific illumination situation within the test region; or/and controlling a light intensity of the light-emitting unit or/and of the light-emitting system; or/and triggering a quality stop of the installation; or/and triggering a supply request.

Switching the emission of test light on and off can comprise a single light-emitting unit or the entire test region. The quality stop of the installation in the present case is understood to mean an interruption of the transport of the objects to be tested through the test region.

A supply request can be issued for example if supply materials that are necessary for testing the objects are running low or need to be replaced.

The embodiment is additionally achieved by way of a light-emitting system for an installation as described above having at least one first and one second light-emitting unit, wherein the first and the second light-emitting units are of identical construction. This has the advantage that the light-emitting units can be produced in cost-effective fashion and a corresponding multitude of possibilities exist within the test region for arranging an operator apparatus. The operator apparatus can also be arranged in any of the light-emitting units, if necessary. At the same time, only one type of light-emitting units needs to be kept in store for replacing the light-emitting units.

The embodiment is additionally achieved by way of a test light module for assembling an installation as described above. The test light module has at least one light-emitting unit, wherein the test light module additionally comprises at least one connection element for at least one line for operating means such that a first test light module can be connected to a second test light module in operation-technology and control-technological terms. In this way, a test chamber can be effectively assembled from a plurality of test light modules and possibly be modified.

BRIEF DESCRIPTION OF THE DRAWINGS

Exemplary embodiments of the invention will be explained below in more detail with reference to the drawings, in which:

FIGS. 3a, 3b, 3c show a detailed view of FIG. 2 with a detail enlargement and a sectional view.

DESCRIPTION OF PREFERRED EXEMPLARY EMBODIMENTS

Figure 1:
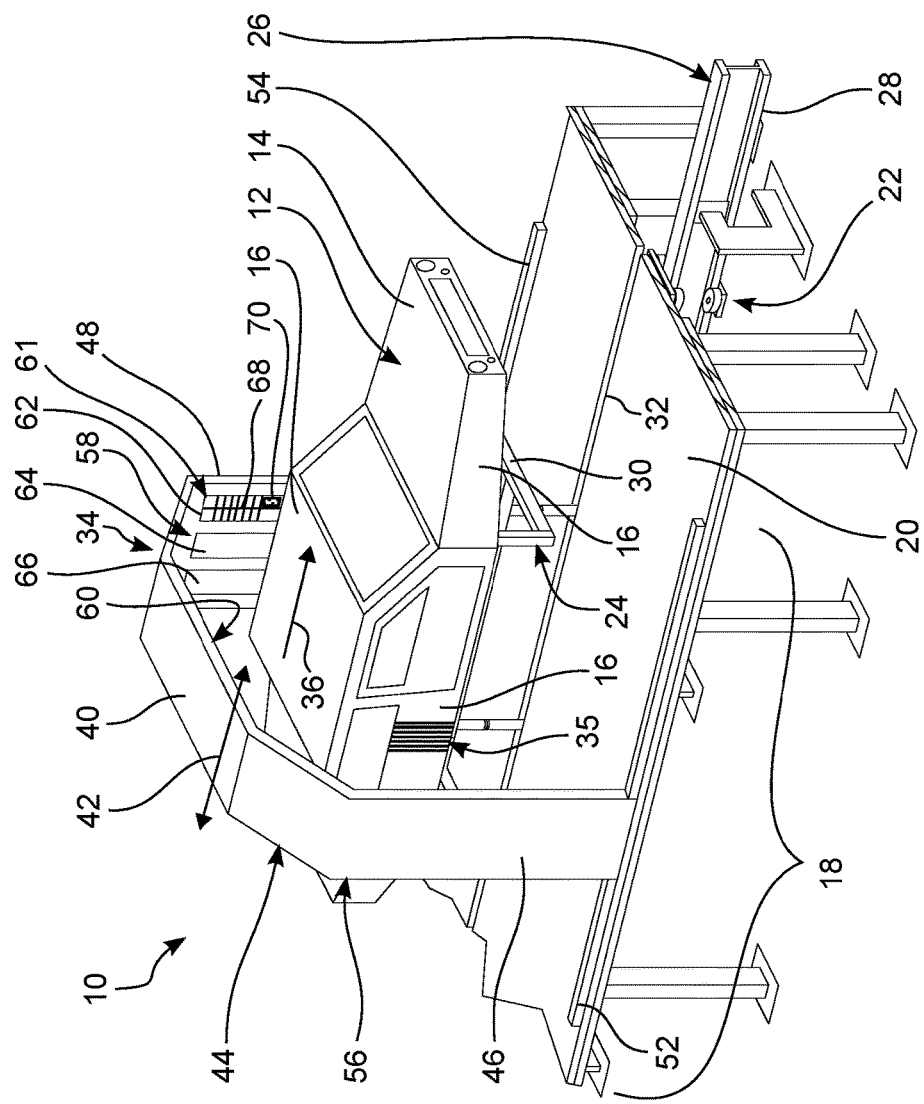
FIG. 1 shows a perspective view of an installation for optically examining surface regions of objects with a movable test light apparatus.

FIG. 1 shows a perspective view of an installation 10 for optically or visually examining surface regions of objects 12. In the present case, vehicle bodies 14 are shown as examples of objects 12. The object 12 shown in FIG. 1 has surface regions 16 to be examined, some of which are provided with a corresponding reference sign. During a test operation, the entire surface of the object 12 is tested by way of an inspector successively checking individual surface regions 16.

In the exemplary embodiment of the installation 10, shown in FIG. 1, the quality of the paint of vehicle bodies 14 is visually inspected by an inspector. To this end, a test zone 18 having a platform 20 on which an inspector may walk is provided in the installation 10. The vehicle bodies 14 are transported into the test zone 18 using a transport system 22.

In the present exemplary embodiment, the transport system 22 comprises a multiplicity of transport carriages 24, on which the vehicle bodies 14 are transported. The transport carriages 24 are displaced on a rail system 26. FIG. 1 shows one of said transport carriages 24.

The rail system 26 comprises a carrier rail 28, on which the transport carriage 24 moves, which carrier rail is embodied in a known manner as an I-profile and is anchored to the platform. The platform-bound carrier rail 28 is of a single-lane type. Alternatively, a multi-lane, in particular a two-lane rail system can of course also be used.

The transport carriage 24 comprises a mounting device 30, on which a vehicle body 14 can be mounted. The mounting device 30 therefore directly accommodates a vehicle body 14, without the vehicle body 14 being mounted on a workpiece carrier, such as a skid.

Alternatively, provision may be made for a transport system in which the vehicle bodies are mounted on workpiece carriers and are transported in this way. This will be explained in more detail below with reference to FIG. 2. Moreover, other conventional suitable transport systems can be used, such as other platform-bound rail systems, suspension rail systems and apron feeders.

The walkable platform 20 of the test zone 18 has a connecting passage 32 that makes possible a connection between the chassis of the transport carriage 24 and the mounting device 30 and thus allows the vehicle bodies 14 to be transported through the test zone 18.

For the assessment of the surface regions 16 of the vehicle body 14, a test light apparatus 34 is provided in the test zone 18, with which the vehicle bodies 14 can be irradiated with test light. A test pattern 35 can be produced in the process, which is movable over a surface region 16 to be examined, as long as the vehicle body 14 is situated in the test zone 18. In principle, the vehicle body 14 should be stationary in the test zone 18 during the test operation. However, the transport system 22 also allows that the vehicle body 14 is moved in the test zone 18 during the test operation.

The test pattern 35 in the present exemplary embodiment is in the form of a stripe pattern, in which light stripes and dark stripes, which are parallel with respect to one another, alternate. The light and dark stripes in the shown exemplary embodiments extend perpendicular to a longitudinal direction 36 of the vehicle bodies 14. The longitudinal direction 36 of the vehicle bodies 14 at the same time corresponds to the transport direction of the vehicle bodies 14.

To produce the test light and the associated test pattern 35, the test light apparatus 34 comprises a light-emitting system, which is supported and carried along by a movable test device 40. The test device 40 is displaceable along a specified trajectory. In the present exemplary embodiment, the test device 40 can be moved in the longitudinal direction 36 of the vehicle body 14 and in the opposite direction. This is illustrated in FIG. 1 by way of a double-headed arrow 42.

The movable test device 40 can be equipped with safety elements for personal safety, such as mechanical switching strips or optical devices such as light barriers.

The test device 40 in the exemplary embodiment shown in FIG. 1 is embodied as a test portal 44 having two vertical supports 46, 48 and a portal arch that connects the vertical supports 46, 48. The vertical supports 46, 48 in principle extend from the bottom upwards, but do not have to exhibit a strictly vertical profile.

The movement of the test device 40 is rail-guided and to this end has, in the present exemplary embodiment, two parallel rails 52, 54, which are fastened to the platform 20 of the test zone 18 and laterally flank the vehicle body 14. The test portal 44 can be moved on the rails 52, 54 by way of a drive. Alternatively, the drive can also be decoupled such that the test portal 44 can also be manually displaced. In this way, it is possible for the test portal 44 for example to be moved manually from one surface region 16 to be tested to the next surface region 16 to be tested. The individual surface region 16 can then be travelled at a specified velocity using a motor.

The test portal 44 carries two side light-emitting devices 56, 58 on its vertical supports 46, 48 and one top light-emitting device 60 at its portal arch. The side light-emitting devices 56, 58 have an identical setup, which is why only the side light-emitting device 58 will be discussed below. The latter comprises a plurality of light-emitting units 62, 64, 66, which are in the form of light-emitting panels 61 and for their part are made from a plurality of light-emitting elements 68. In the present exemplary embodiment, each side light-emitting device 56, 58 has four light-emitting units 62, 64, 66 in a 3×2 arrangement. Other arrangements can also easily be realized. Alternatively, only one light-emitting panel may be provided.

In the exemplary embodiment shown in FIG. 1, each light-emitting unit 62, 64, 66 comprises a plurality of light-emitting elements 68, which for their part can each have, for example, four individual light-emitting means—for example LEDs. The individual light-emitting means can be, for example, white light-emitting diodes, yellow light-emitting diodes or/and RGB light-emitting diodes.

The white light-emitting diodes can exhibit, for example, a light temperature of 6500 K and produce what is known as daylight white. The yellow light-emitting diodes can have a temperature of 2700 K and produce what is known as warm white. If the light emitted by the white light-emitting diodes and the yellow light-emitting diodes is mixed to equal proportions, a light temperature of 4000 K is obtained, which is also referred to as cold white, or neutral white. This light temperature is not very tiring for the human eye.

The top light-emitting device 60 is set up in a manner corresponding to the side light-emitting device 58 and likewise comprises a plurality of light-emitting units.

The light-emitting elements 68 of the individual light-emitting units 62-66 both of the side light-emitting devices 56, 58 and of the top light-emitting device 60 can be selectively activated and deactivated independently of the remaining light-emitting elements or/and light-emitting panels. For example, specific surface regions 16 of the vehicle bodies 14 can be selectively irradiated with test light and a test pattern 35.

The light-emitting panels 61 that are not required for producing the test pattern 35 can be used to provide general illumination of the test zone 18 or of the region under the test portal 44, if this is necessary. To this end, the light intensity in the individual light-emitting elements 68 can be selectively reduced or increased to the required extent. A basic illumination of the test zone 18 can moreover be ensured for example by way of light-emitting units in the platform 20 of the test zone 18.

As can already be seen in the illustration of FIG. 1, the light-emitting unit 62 has, in addition to the light-emitting elements 68, an operator apparatus 70. The setup and the function of the operator apparatus 70 will be explained in more detail below with reference to FIG. 3.

Figure 2:
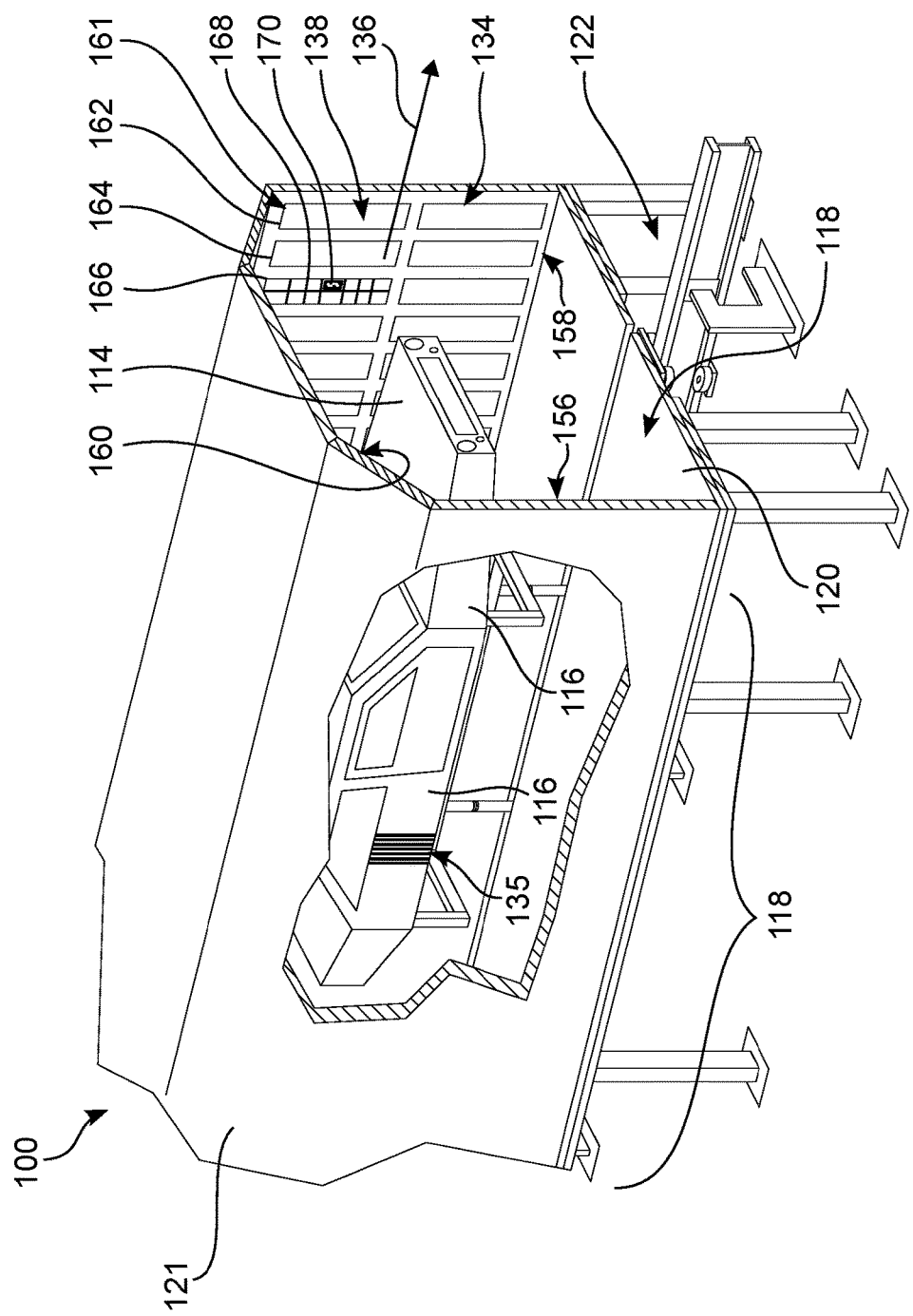
FIG. 2 shows a perspective view of an installation for optically examining surface regions of objects, in which objects are transported through a test chamber using a transport system.

FIG. 2 shows a perspective view of an installation 100 for optically examining surface regions of objects 12. Features that are identical or comparable to the features of the embodiment shown in FIG. 1 carry reference signs in the embodiment of FIG. 2 that are increased by 100. To avoid repetition, only the features that have relevant differences are described.

The installation 100 comprises a test region 118 having a housing 121. Vehicle bodies 114 can be transported through the housing 121 using a transport system 122. The transport system 122 of the embodiment shown in FIG. 2 is comparable to the transport system 22 that is shown in FIG. 1. Alternatively, the transport system 122 could for example also be in the form of a roller conveyor, on which what are known as skids can be transported. Placed in the test region of the installation 100, which region is in the form of a test chamber 118 in the exemplary embodiment and can be referred to as a light tunnel, is a test light apparatus 134, which largely has the same construction as the test light apparatus 34 of the exemplary embodiment in FIG. 1.

The important difference is that the test light apparatus 134 is stationary and not movable. The light-emitting system 138 of the test light apparatus likewise comprises two side light-emitting devices 156, 158 and one top light-emitting device 160. In contrast to the embodiment of FIG. 1, the side light-emitting devices 156, 158 and the top light-emitting device 160 extend over the entire test region and thus form the test chamber 118, or the light tunnel.

As already described above with respect to the exemplary embodiment of FIG. 1, the light-emitting units 162-166, which are embodied as light-emitting panels 161, have a multiplicity of light-emitting elements 168. The light-emitting unit 166 comprises not only the multiplicity of light-emitting elements 168, but also an operator apparatus 170. The detailed setup and function of the latter will be explained below with reference to FIG. 3.

FIG. 3a shows a section of FIG. 2, FIG. 3b shows an enlarged section from FIG. 3a. FIG. 3c shows a cross-sectional view along the line c-c of FIG. 3b from the view of the test region.

The operator apparatus 170 has a multiplicity of capacitive sensors 172, 174. The capacitive sensors 172, 174 are arranged on that side of a protective cover 171, which may for example be made of glass, that is remote from the test tunnel 118. Each of the capacitive sensors 172, 174 can produce a signal that indicates operation of the operator apparatus 170.

The protective cover 171 of the light-emitting panel 161 has, in the region of the operator apparatus 170, a blackened area 176. The blackened area can be provided inside the protective cover 171, on the rear side of the protective cover 171 (that is to say the side that is remote from the test region and on which the capacitive sensors 172, 174 are arranged) or on the outside of the protective cover 171 (that is to say on the side that faces the test region). Control fields 178 exhibit contrasting colour. The control fields 178 can be provided, in the same way as the blackened area 176, on the outside of, the inside of or in the protective cover 171 itself.

The capacitive sensors 172, 174 are assigned different functions. A first group 173 of sensors 172 forms on/off buttons. Upon actuation of the sensors 172, the correspondingly actuated light-emitting unit 166 is switched on or off.

A second group 175 of sensors 174 forms a key pad via which for example numeric codes for identifying the inspector that is actuating it can be input. The inputs made via the second group 175 can be represented for example on a display 180. At the same time, or alternatively, the display 180 can display information relevant for the operator during the test operation, such as data relating to the vehicle body 14 to be tested or/and its paint etc.

In this way, the operator apparatus 170 forms a decentralized control and operating unit that is integrated in the light-emitting unit 166. The operator apparatus 170 can be designed for a light-emitting unit 166 and be provided only for operating this one operator apparatus. Alternatively, it is possible for a plurality of light-emitting units to be able to be operated via the operator apparatus 170.

Different functions may be triggered via the operator apparatus 170. By way of example, in addition to the already mentioned on/off function, a specific light scenario, a light colour and/or a light intensity of an individual module, of a plurality of modules or of all modules of the test region can be controllable, settable or/and activatable.

The plurality of groups of sensors can also be grouped by way of a common housing. In one variant, the operator side of the operator apparatus is freely configurable with respect to appearance and function.

In addition to the light-related settings, other functions can be triggerable or actuable via the operator apparatus 170, such as for example a quality stop of the transport system 122 or a request for supply materials, in order to ensure an improved work sequence in the painting installation, or the light tunnel.

The signal that is recorded or produced by the operator apparatus 170 can be passed on to a control board of the light-emitting unit and be processed there. Next, a corresponding action can be triggered. It is possible for example for decentralized control of the light-emitting unit 166 to be performed. It is also possible for a multiplicity of light-emitting units to be actuated by way of the signal, which is recorded in decentralized fashion, by central processing of the signals for example using a control center. The control center receives and then transmits signals that in turn can be commands or information or error messages.

Possible in this way are decentralized control of the individual light-emitting unit, partially central control of a plurality of light-emitting units, and central control of all light-emitting units, and also activation of other processes, for example by the individual operator apparatus itself or from a control center.

Activation of such a signal at the operator apparatus can be made dependent for example on a specific minimum time stored to prevent the triggering of false signals. Other safety precautions are possible.

Further functions can be integrated without difficulty without changing the design of the light tunnel.

The invention claimed is:

1. An installation for optically examining surface regions of objects, in particular of painted vehicle bodies, the system comprising:
   a test light apparatus for irradiating an object, situated in a test region of the installation, with test light and/or for producing a test pattern on the surface region;
   wherein the test light apparatus has a light-emitting system having a plurality of light-emitting units for emitting test light into the test region, wherein the light-emitting units have a transparent cover with respect to the test region; and
   an operator apparatus arranged, as viewed from the test region, behind the transparent cover and set up such that by touching at least one section of the cover, operation of the operator apparatus can be effected.

2. The installation of claim 1, wherein the operator apparatus comprises a capacitive sensor.

3. The installation of claim 1, wherein the operator apparatus is arranged in a region of the light-emitting unit which is not intended for the emission.

4. The installation of claim 1, wherein the operator apparatus has a display field, which is arranged behind the transparent cover and is set up for displaying information relevant for operating the operator apparatus.

5. The installation of claim 1, wherein the operating element is designed such that, by operating the operating element:
   the emission of test light into the test region is able to be switched on and off;
   a specific illumination situation within the test region is activatable;
   a light intensity of the light-emitting unit and/or of the light-emitting system is controllable;
   a quality stop of the installation is triggerable; and/or
   a supply request is triggerable.

6. A light-emitting system for the installation of claim 1, the light-emitting system having at least one first light-emitting unit and one second light-emitting unit, wherein the light-emitting units are of identical construction.

7. A test light apparatus for assembling with the installation of claim 1.

* * * * *